(12) United States Patent
Buge et al.

(10) Patent No.: US 10,449,175 B2
(45) Date of Patent: Oct. 22, 2019

(54) RINSE-OFF CHEMICAL MOUSSE CONTAINING BENZOYL PEROXIDE

(71) Applicant: GALDERMA RESEARCH & DEVELOPMENT, Biot (FR)

(72) Inventors: Jean-Christophe Buge, Nice (FR); Karine Nadau-Fourcade, Villeneuve Loubet (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 15/300,040

(22) PCT Filed: Mar. 27, 2015

(86) PCT No.: PCT/EP2015/056783
§ 371 (c)(1),
(2) Date: Sep. 28, 2016

(87) PCT Pub. No.: WO2015/144905
PCT Pub. Date: Oct. 1, 2015

(65) Prior Publication Data
US 2017/0172972 A1    Jun. 22, 2017

Related U.S. Application Data

(60) Provisional application No. 61/971,658, filed on Mar. 28, 2014.

(51) Int. Cl.
| | | |
|---|---|---|
| *A61K 31/327* | (2006.01) | |
| *A61K 8/04* | (2006.01) | |
| *A61K 9/12* | (2006.01) | |
| *A61K 8/19* | (2006.01) | |
| *A61K 47/02* | (2006.01) | |
| *A61K 9/46* | (2006.01) | |
| *A61K 8/38* | (2006.01) | |
| *A61Q 19/10* | (2006.01) | |
| *A61K 9/00* | (2006.01) | |
| *A61K 45/06* | (2006.01) | |
| *A61K 47/36* | (2006.01) | |
| *A61K 8/365* | (2006.01) | |
| *A61K 8/73* | (2006.01) | |
| *A61K 47/12* | (2006.01) | |

(52) U.S. Cl.
CPC ............ *A61K 31/327* (2013.01); *A61K 8/046* (2013.01); *A61K 8/19* (2013.01); *A61K 8/365* (2013.01); *A61K 8/38* (2013.01); *A61K 8/73* (2013.01); *A61K 9/0007* (2013.01); *A61K 9/0014* (2013.01); *A61K 9/12* (2013.01); *A61K 9/122* (2013.01); *A61K 45/06* (2013.01); *A61K 47/02* (2013.01); *A61K 47/12* (2013.01); *A61K 47/36* (2013.01); *A61Q 19/10* (2013.01); *A61K 2800/22* (2013.01); *A61K 2800/222* (2013.01); *A61K 2800/882* (2013.01)

(58) Field of Classification Search
CPC combination set(s) only.
See application file for complete search history.

(56) References Cited

U.S. PATENT DOCUMENTS

| | | | |
|---|---|---|---|
| 6,177,092 B1 * | 1/2001 | Lentini | ................. A61K 8/046 424/401 |
| 2005/0123487 A1 * | 6/2005 | Spadini | .................... A61K 8/22 424/47 |
| 2007/0237724 A1 | 10/2007 | Abram et al. | |
| 2009/0191248 A1 | 7/2009 | Hoffman et al. | |
| 2009/0214628 A1 | 8/2009 | De Rijk et al. | |
| 2013/0317108 A1 | 11/2013 | At | |
| 2013/0338230 A1 | 12/2013 | At | |
| 2013/0338235 A1 | 12/2013 | At | |

FOREIGN PATENT DOCUMENTS

| | | |
|---|---|---|
| DE | 10 2008 029 357 A1 | 12/2009 |
| EP | 1 043 023 A1 | 10/2000 |
| WO | 20000027356 A1 | 5/2000 |
| WO | 20050058272 A1 | 6/2005 |
| WO | WO-2009/069006 A2 | 6/2009 |
| WO | WO-2012/085480 A1 | 6/2012 |
| WO | WO-2012/085481 A1 | 6/2012 |
| WO | WO-2012/085483 A1 | 6/2012 |

OTHER PUBLICATIONS

Anonymous, "Benzefoam Ultra", Drug Information Online—Drugs. com, Apr. 3, 2011, pp. 1-9, XP 002739766.
International Search Report corresponding to International Patent Application No. PCT/EP2015/056783, dated Jul. 7, 2015, with English translation, 6 pages.
International Search Report of International Patent Application No. PCT/EP2015/056784 dated Jun. 8, 2015. 7 pages.
International Search Report of International Patent Application No. PCT/EP2015/056785 dated Jun. 5, 2015. 7 pages.

* cited by examiner

*Primary Examiner* — Bethany P Barham
*Assistant Examiner* — Peter Anthopolos
(74) *Attorney, Agent, or Firm* — Foley & Lardner LLP; Sunit Talapatra

(57) ABSTRACT

A composition is described for a topical application, in the form of a rinse-off mousse, including no or only a small quantity of foaming surfactants. The composition can include a medium that is cosmetically or pharmaceutically compatible with a topical application, and benzoyl peroxide. The composition can also include at least one intermediate composition, at least one gas-generating agent, at least one agent activating the at least one gas-generating agent, and benzoyl peroxide. A kit or a single container with a plurality of compartments including this composition is also described.

32 Claims, 2 Drawing Sheets

RINSE-OFF CHEMICAL MOUSSE CONTAINING BENZOYL PEROXIDE

CROSS-REFERENCE TO PRIOR APPLICATIONS

This application is a National Stage of PCT/EP2015/056783, filed Mar. 27, 2015, and designating the United States (published Oct. 1, 2015, as WO 2015/144905 A1), which claims priority under 35 U.S.C. § 119 to U.S. Provisional Application No. 61/971,658, filed Mar. 28, 2014, hereby expressly incorporated by reference in its entirety and each assigned to the assignee hereof.

A subject matter of the present invention is a rinse-off topical cleaning product in the form of a foam for the cosmetic and/or pharmaceutical treatment of skin suffering from acne comprising benzoyl peroxide in dispersed form.

Despite new generations of foaming surfactants, hygiene products and particularly cleaning products remain irritating and can result in mediocre tolerance of the product. However, the user associates the volume and the amount of foam with the cleaning power and with the effectiveness of the latter. There thus exists a need to develop new foaming pharmaceutical dosage forms containing few or no foaming surfactants which simultaneously are effective and meet the expectations of the user, while improving the tolerance of this type of product.

For many years, BPO or benzoyl peroxide, of formula $C_{14}H_{10}O_4$, has been a therapeutic agent recommended in the treatment of acne. First of all, the effectiveness of benzoyl peroxide is related to its decomposition when it is brought into contact with the skin. This is because it is the oxidizing properties of the free radicals produced during this decomposition which result in the desired effect. Consequently, in order to keep the benzoyl peroxide at an optimum effectiveness, it is important to prevent it from decomposing before use, that is to say during storage.

However, benzoyl peroxide is an unstable chemical compound, which makes it difficult to formulate it in finished products. In addition, BPO exhibits a cross-reactivity with the other ingredients normally employed in topical formulations which either limits the use thereof or requires that other pharmaceutical dosage forms be found. Mention may be made, by way of example, of the reactivity of BPO in the presence of surfactants in the composition. Furthermore, BPO is particularly recognized as being tolerated with difficulty by consumers following an anti-acne treatment. This tolerance with regard to BPO is highly variable depending on the formulation used as vehicle.

Thus, there therefore exists the need to have available novel pharmaceutical dosage forms of foaming cleaning product in which the benzoyl peroxide is stable, well tolerated, effective and pleasant to apply.

This is because, generally, the foaming compositions contain a large amount of foaming surfactants. This high content causes skin irritation. The present invention is targeted at providing a composition which is particularly well tolerated, as is shown by the examples illustrating one of the methods for evaluating the tolerance which are presented below.

Various methods exist for evaluating the tolerance of a pharmaceutical or cosmetic product for cutaneous use, among which may be mentioned the in vivo "in used" or "human patch test" test but also the in vitro test, such as the test for measurement of the irritation on Reconstructed Human Epidermis (RHE) described in the OECD TG 439 protocol. The latter method is described in detail in example 3.

Cleaning foams or foaming compositions currently exist on the market. However, they all exhibit a certain number of disadvantages.

Indeed there exist four types of cleaning foams or foaming compositions:

- Aerosols, in which the foam is generated by a propellant gas but with the disadvantage of being aerosols exhibiting the well-known risks of the latter (contamination, breathing risks in particular).
- Formulations rich in foaming surfactants. These formulations exhibit the disadvantage of being in the best of cases slightly irritating; generally they are irritating. Furthermore, the active principles sensitive to the presence of foaming surfactants in a fairly high amount cannot be envisaged in this type of composition.
- Rinsable whipped creams, in which air bubbles are introduced into the product by virtue of a specific manufacturing process. This manufacturing process exhibits the disadvantage of being very restricting at the industrial level and requires a major capital cost with regard to the industrial packaging equipment.
- Foaming formulations which are low in foaming surfactants but are packaged in a packaging provided with a mechanical foam-generating system (pump with screen of Pulvorex type). This type of formulation exhibits the disadvantage of not being compatible with the use of active principles in the dispersed form.

Thus, the need therefore remains to develop a cosmetic or pharmaceutical composition, the pharmaceutical dosage form of which is different from the known pharmaceutical dosage forms, in order to overcome their disadvantages and to thus make possible the use of BPO in the dispersed form in well-tolerated rinsable cleaning foaming compositions intended for topical application to human beings.

The aim of the present invention is thus to provide such a composition which meets these needs.

The applicant company has thus developed a new cosmetic and/or pharmaceutical composition intended for rinse-off topical application which is provided in the form of a foam with little or no foaming surfactant, that is to say with a content of foaming surfactant which is advantageously less than or equal to 1% by weight of active material. Foaming surfactant is understood to mean surfactants which produce a voluminous, stable and creamy foam when they are mixed with water according to tests well-known to a person skilled in the art.

The following in particular constitute foaming surfactants: anionic surfactants, cationic surfactants, amphoteric surfactants and nonionic surfactants of the family of the alkylpolyglucosides and glucamides.

The pharmaceutical dosage form according to the invention exhibits the advantage of guaranteeing good stability of the BPO. Furthermore, this formulation advantageously results in a mild, perfectly tolerated and non-irritant foam being obtained, which makes it possible to treat and clean skin suffering from acne while overcoming the problems of tolerance and while satisfying the client as regards foam quality.

Finally, advantageously, this pharmaceutical dosage form does not require, for the employment thereof, the use of propellant gases or aerosols. Thus, "aerosol" or "spray" foams are excluded from the scope of the invention. Likewise, the rinsable foaming compositions of the prior art of the type of conventional foaming compositions rich in foaming surfactants and/or foaming formulations having a smaller content of surfactants but requiring a mechanical foam-generating system (Pulvorex type) are also excluded from the invention. It is the same for the foaming compositions involving a whipping process.

Finally, a subject matter of the present invention is the cosmetic use of the composition according to the invention, by topical application of this composition to the skin, and also a medicament intended for topical application to the skin, comprising such a composition. According to the invention, after its application, the composition according to the invention is removed by rinsing.

BRIEF DESCRIPTION OF THE DRAWING

The present invention will be described in more detail in the description and examples below, and in the light of the figures appended to the present patent application.

Figure 1:
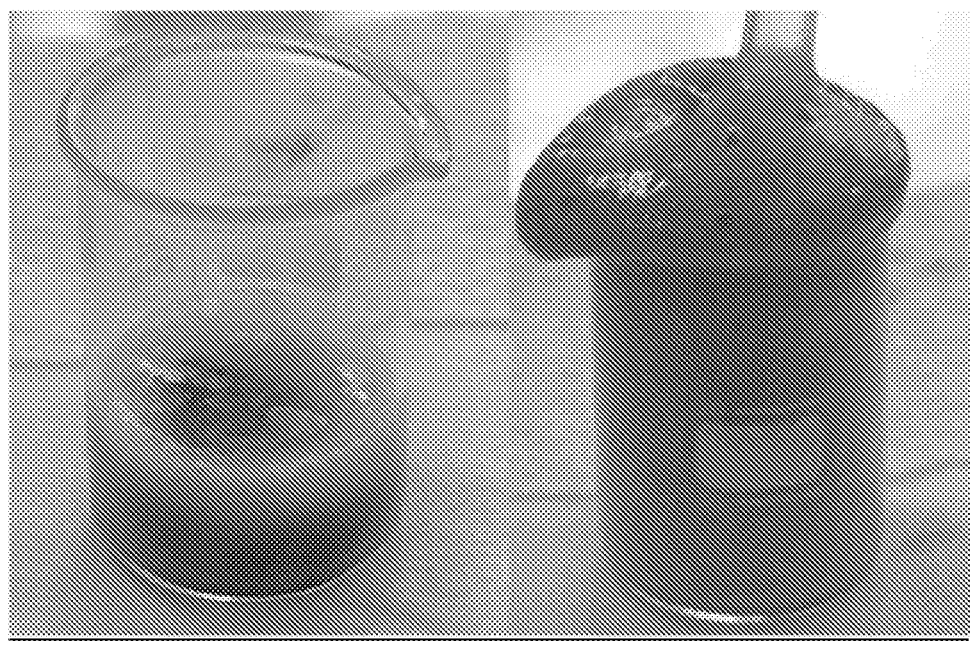
FIG. 1 shows photographs of a first composition in accordance with the invention obtained by mixing the two intermediate compositions A5 and B1 described in the examples, immediately after mixing these compositions and then when the reaction between these two compositions is complete (maximum volume of foam).

This composition is capable of taking the form of a foam due to its composition alone and can thus also be defined as a self-foaming composition for topical application.

A first subject matter of the present invention is consequently a composition comprising benzoyl peroxide intended for a topical application which is provided in the form of a foam, advantageously with a semisolid consistency, with little or no foaming surfactant (content of less than or equal to 1% by weight, with respect to the weight of the total composition), comprising a medium cosmetically or pharmaceutically compatible with a rinse-off topical application, in particular to the skin.

Composition which is provided in the form of a foam (also referred to below as self-foaming composition) is understood to mean a composition with a semisolid consistency having an aerated form comparable to a foam.

The present self-foaming composition comprises at least the ingredients below:
  at least one intermediate composition or formulation,
  at least one gas-generating agent,
  at least one agent which activates the gas-generating agent, and benzoyl peroxide.

In a preferred aspect, the self-foaming composition comprises at least two intermediate compositions or formulations in variable proportions and in particular the ingredients below:
  at least one intermediate composition or formulation A,
  at least one intermediate composition or formulation B,
  at least one gas-generating agent,
  at least one agent which activates the gas-generating agent,
  benzoyl peroxide present in at least one of the intermediate compositions.

Preferably, the gas-generating agent is present in one of the abovementioned intermediate formulations.

In an even more preferred aspect, the self-foaming composition comprises at least two intermediate compositions or formulations in variable proportions and in particular the ingredients below:
  at least one intermediate composition or formulation A which comprises an agent which activates the gas-generating agent,
  at least one intermediate composition or formulation B which comprises a gas-generating agent,
  benzoyl peroxide present in at least one of said intermediate formulations A and B.

Preferably, the benzoyl peroxide is present in the intermediate composition A.

The composition according to the invention is self-foaming, that is to say that it foams by simple mixing of the intermediate compositions A and B.

Depending on the agents present in the intermediate composition (or intermediate formulation), and also on their proportions in said composition, the latter can be provided in all the pharmaceutical dosage forms or take all the known textures which can be used in cosmetics and/or in pharmaceuticals, for a topical application.

Preferably, each intermediate composition (or intermediate formulation) according to the invention can thus be provided, for example, in the form of a gel, emulsion (cream, surfactant-free cream, lotion, milk or fluid cream), serum, solution or suspension and preferably in the form of an emulsion (cream, surfactant-free cream, lotion, milk or fluid cream) or a gel. All these formulations come within the definition of the foaming composition in the context of the invention.

According to the invention, each intermediate composition (or formulation) can exhibit a viscosity (measured at 25° C. and at atmospheric pressure) of between 1 cP and 500 000 cP, advantageously between 500 cP and 350 000 cP, measured with a conventional method of Brookfield RV DV-II type: spindle 6, speed 2.

According to the invention, the gas generated by the gas-generating agent can be any physiologically compatible gas which makes it possible to obtain a foam, such as, for example, carbon dioxide ($CO_2$) or oxygen ($O_2$).

According to the invention, it being possible for the gas concentration to vary, the amount of bubbles in the composition can vary and can thus give a composition which can range from poorly aerated to very strongly aerated.

According to the invention, agent which activates the gas-generating agent is understood to mean an ingredient which, by chemical reaction with the gas-generating agent, releases a gas. Preferably, an acid/base reaction is involved.

Thus, according to the invention, the self-foaming composition can preferably be provided in all the forms ranging from aerated to a highly expanded foam.

The composition according to the invention is suitable for topical application and can in addition comprise a physiologically acceptable medium, that is to say a medium compatible with the skin and superficial body growths. It is preferably a cosmetically or pharmaceutically acceptable medium.

In addition, the composition can comprise any active agent capable of exhibiting an optionally therapeutic activity. These active agents can, inter alia, be chosen from emollients, humectants, agents for combating free radicals, anti-inflammatory agents, vitamins, depigmenting agents, antiacne agents, antiseborrheic agents, antifungal agents, keratolytic agents, sunscreens, slimming agents or skin-coloring agents.

The composition according to the invention can comprise, in addition to the abovementioned active principles, cosmetically and/or pharmaceutically acceptable adjuvants, such as dispersing agents, solubilizing agents, stabilizing agents, preservatives, fatty phases, fatty substances, thickening agents, dyes, fragrances, nonfoaming surfactants, gelling agents, complexing agents, neutralizing agents, odor maskers, fillers, sequestering agents, reducing agents, plasticizing agents, softening agents, moisturizing agents, pigments, clays, inorganic fillers, inorganic colloids, polymers, proteins, pearlescent agents, waxes, oils, such as, for example, paraffins, fatty acids, solid esters of fatty alcohol or of fatty acids, gums or wetting agents.

Of course, a person skilled in the art will take care to choose this or these optional additional adjuvants and/or their amounts so that the properties of the active principle(s) which can be added to the composition according to the invention are not, or not substantially, detrimentally affected by the envisaged addition.

Dyes, such as FD&C Blue 1, can also be present in at least one of the intermediate compositions. Such dyes exhibit the advantage of coloring one of the formulation intermediates. This coloring makes it possible to monitor the satisfactory mixing of the two formulation intermediates and to set off the formation of the foam.

According to the invention, the self-foaming composition (that is to say, ready-to-be-applied composition) can have a pH of between 2 and 8, preferably between 3 and 7.

Insofar as the intermediate composition(s) (or formulation(s)) require storage in at least 2 compartments for reasons of stability of the ingredients, the present invention relates either to a single compartmentalized container (each compartment containing one intermediate formulation) preferably comprising 2 or 3 compartments or to a kit comprising each intermediate formulation stored independently from one another and physically separated. The intimate mixing at the time of use (directly on the skin or on any other support) of the intermediate formulations makes it possible to obtain the self-foaming composition according to the invention.

More specifically, the intermediate composition (or formulation) A can be provided in the form of a solution, an emulsion (lotion, cream, emulsifier-free cream, milk, fluid cream) or a gel. This composition advantageously comprises the agent which activates the gas-generating agent, preferably an acid, in a sufficient amount (which can be provided in the form of an acid/base buffer at acidic pH), which can be, as nonlimiting example, the citric acid/sodium citrate pair.

The formulation B can be provided in the form of a solution, a gel or an emulsion (lotion, cream, emulsifier-free cream, milk, fluid cream). This composition advantageously comprises, in a sufficient amount, a gas-generating agent which can in particular be sodium bicarbonate.

Thus, another subject matter of the invention is a kit or a single multicompartment container as defined above, making possible the preparation at the time of use of a self-foaming composition according to the invention, separately comprising at least two intermediate formulations (or intermediate compositions):
  an intermediate formulation A comprising at least one agent which activates the gas-generating agent; and
  an intermediate formulation B comprising at least one gas-generating agent;
  benzoyl peroxide being present in at least one of said intermediate formulations A and B.
Preferably, the benzoyl peroxide is present in the intermediate composition A.

Gas-Activating Agent:

The agent which activates the gas-generating agent (also denoted by "gas-activating agent") is a compound which reacts with the gas-generating agent by a chemical reaction (preferably an acid/base reaction) which releases a gas.

It is advantageously an acid, a partially salified polyacid salt or else a buffer solution of weak acid and of its conjugate base, or a mixture of such compounds.

According to the invention, the acid/base buffer of said acid can be any acid/base buffer of the weak acid, such as, for example, a citric acid/sodium citrate buffer or else a tartaric acid/sodium tartrate buffer. Mention will preferably be made of α-hydroxy acids, which are weak acids preferably having a pKa of between 2 and 6, such as citric acid, tartaric acid, malic acid or lactic acid, but also phosphoric acid and pyrophosphoric acid and their partially salified salts, such as disodium pyrophosphate or sodium dihydrogenphosphate, also known as monosodium phosphate.

Preferably, according to the invention, the gas-activating agent is chosen from a citric acid/sodium citrate buffer alone, phosphoric acid, sodium phosphate, disodium pyropyrophosphate, which are alone or as a mixture with the citric acid/sodium citrate buffer. According to a very preferred embodiment, the gas-activating agent is a citric acid/sodium citrate buffer, alone or as a mixture with sodium phosphate and/or disodium pyrophosphate.

In compositions for sensitive skin or for damaged skin, such as skin suffering from acne, the content of citric acid/sodium citrate is preferably less than or equal to 2.4%, with respect to the total weight of the intermediate composition A, so as to limit any risk of tingling. In order to improve the tolerance and to avoid the sensation of tingling, preferably, the citric acid/sodium citrate buffer is employed as a mixture with disodium pyrophosphate or sodium dihydrogenphosphate.

According to the invention, said gas-activating agent can be present in the intermediate formulation A in an amount which can range from 0.001% to 95% by weight, with respect to the total weight of the intermediate formulation A.

Gas-Generating Agent:

Gas-generating agent is understood to mean any agent which has the property of generating a gas by a chemical reaction. Mention will be made, in this regard, of any compound which, when it is mixed with a weak acid, can form a gas by a chemical reaction equivalent to the following:

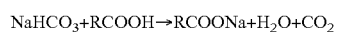

$$NaHCO_3 + RCOOH \rightarrow RCOONa + H_2O + CO_2$$

According to the invention, the gas generated from the gas-generating agent present in the intermediate composition B is preferably carbon dioxide ($CO_2$).

According to the invention, the gas-generating agent is preferably chosen from sodium bicarbonate, potassium bicarbonate, sodium carbonate, potassium carbonate and their mixtures.

Preferably, according to the invention, the intermediate formulation B comprises an agent which generates carbon dioxide, which agent is particularly preferably sodium bicarbonate.

Said gas-generating agent can be present in the intermediate formulation B in an amount ranging from 1% to 10% by weight, preferably from 2% to 8% by weight, with respect to the weight of the formulation B.

According to the invention, the intermediate formulation A can exhibit an acidic pH, advantageously of between 1 and 6, and the intermediate formulation B can exhibit a basic pH, advantageously of between 7 and 12.

According to the invention, one (or the) intermediate formulation(s) A and B described above comprises benzoyl peroxide in an amount ranging from 0.0001% to 20% of benzoyl peroxide, preferably from 0.025% to 10%, more preferably still from 2.5% to 5%, by weight, with respect to the weight of the total composition.

In the present description, total composition or total formulation is understood to mean the composition of the product in the form of a foam after said intermediate compositions have been mixed. Preferably, the BPO is present in the composition A at an acidic pH in order to optimize its stability.

The intermediate formulation A can be provided in all the pharmaceutical dosage forms compatible with the pharmaceutical dosage form desired for the final composition obtained by mixing the formulation A with the formulation B. Advantageously, the formulation A can be a gel, a solution, a suspension or an emulsion (cream, surfactant-free cream, lotion, milk, fluid cream), preferably a gel guaranteeing the suspension and the stability of the BPO. According to a particularly preferred embodiment, the intermediate formulation A is a gel.

The intermediate formulation B can be provided in all the pharmaceutical dosage forms compatible with the pharmaceutical dosage form desired for the final composition obtained by mixing the formulation B with the formulation A. Advantageously, the formulation B can be a gel, a solution, a suspension or an emulsion (cream, surfactant-free cream, lotion, milk, fluid cream), preferably a gel, a solution or an emulsion. According to a particularly preferred embodiment, the intermediate formulation B is an emulsion and comprises a fatty phase comprising one or more oils, as are described below.

Each formulation of the kit or of the multicompartment container as defined above in accordance with the invention comprises a physiologically acceptable medium which conveys the compound or compounds and is chosen so that the compounds are capable of reacting with one another in order to form a self-foaming composition during the mixing of at least the intermediate formulations A and B.

Thus, the mixing at the time of use of at least two formulations, for example the formulation A and the formulation B, creates the self-foaming composition according to the invention.

During the mixing of the two formulations A and B, the gas-generating agent, such as sodium bicarbonate, can react with the gas-activating agent, such as the acid, and thus give in particular the salt corresponding to the acid, water and $CO_2$ gas. It is this gas, trapped in the bubbles of the composition, which creates the foam which characterizes the self-foaming composition of the invention.

Thus, by the mixing of at least the intermediate formulation A and the intermediate formulation B, the foam composition, referred to as total composition, according to the invention is obtained.

Unreacted gas-activating agent and/or gas-generating agent may, of course, remain in the composition obtained after mixing at least the formulations A and B.

Advantageously, the kit or the single multicompartment container according to the invention can be designed so that, during the preparation of the composition according to the invention, the intermediate formulations A and B can be mixed in an A/B ratio by weight ranging from 0.5 to 2, preferably from 0.5 to 1.5, more preferably of approximately 1 (that is to say, from 0.9 to 1.1) and more preferably still of 1. This means that the kit can be designed in order to simultaneously release doses (by weight) of the intermediate compositions A and B which can be in a ratio by weight ranging from 2 doses of B per 1 dose of A to 2 doses of A per 1 dose of B, preferably from 2 doses of B per 1 dose of A to 3 doses of A per 2 doses of B. According to a preferred embodiment of the invention, the kit is designed in order to simultaneously release 1 dose by weight of A and 1 dose by weight of B.

According to the invention, the kit can be provided in any form compatible with, on the one hand, separate storage of the intermediate formulations A and B and, on the other hand, the ability to carry out the mixing of A and B at the time of use.

For example, the intermediate formulations A and B can be in a case with at least two separate compartments, each comprising A or B.

According to another aspect, the kit can be provided in the form of a syringe having at least two separate bodies, each provided with a piston, said two bodies comprising A and B and being designed in order to simultaneously release, by the exercise of a force on the piston, the desired doses of A and B.

The invention also relates to a process for the preparation of a composition according to the invention, characterized in that, in order to obtain the self-foaming composition, at least one dose of intermediate formulation A and one dose of intermediate formulation B of the kit as are defined above are mixed at the time of use in relative proportions by weight A/B which can range from 0.5 to 2, preferably from 0.5 to 1.5 and more preferably of 1.

In order to obtain an optimum foam (final composition), the inventors have searched experimentally for the optimum contents of gas-generating agent (preferably sodium bicarbonate) and of gas-activating agent (preferably citric acid and/or disodium pyrophosphate and/or sodium dihydrogenphosphate).

Thus, it has been determined experimentally that, when the gas-activating agent is citric acid, the citric acid/sodium bicarbonate ratio by weight in the total composition is between 0.1 and 2, preferentially between 0.5 and 1 and preferably equal to 0.7.

In the same way, it has been determined that, when the gas-activating agent is disodium pyrophosphate, the disodium pyrophosphate/sodium bicarbonate ratio by weight in the total composition is between 0.5 and 5, preferentially between 1 and 3 and preferably is equal to 2.4.

In the same way, it has been determined that, when the gas-activating agent is sodium dihydrogenphosphate, the sodium dihydrogenphosphate monohydrate/sodium bicarbonate ratio by weight in the total composition is between 0.5 and 5, preferentially between 1 and 3 and preferably is equal to 2.

The sodium bicarbonate/citric acid, sodium bicarbonate/sodium pyrophosphate and sodium bicarbonate/sodium hydrogenphosphate ratios are exemplified in example 4.

Surprisingly, the combination formed of citric acid/sodium citrate, disodium pyrophosphate and a gelling system compatible with the pharmaceutical dosage form has made it possible to obtain a formulation with very stable physicochemical properties (see table I) and in which the BPO is particularly stable (see table II), which does not generate any unpleasant sensation on the skin and which makes possible the release of gas and thus the creation of foam.

A composition is regarded as physically stable when its organoleptic characteristics, its pH, its viscosity and the homogeneity of the BPO do not change over time under different temperature conditions: ambient temperature (AT), 30° C. and 40° C.

According to the invention, ambient temperature corresponds to a temperature ranging from 15° C. to 25° C.

TABLE I

Physical stability of the intermediate formulation A5 (example 1) comprising BPO

| Formulation A5 | T0 | | T3 Months | | T6 Months | |
|---|---|---|---|---|---|---|
| pH | 3.54 | 25° C. | 4.0 | | — | |
| | | 30° C. | 4.0 | | — | |
| | | 40° C. | 4.0 | | — | |
| Viscosity cP Brookfield RV DVII | Spindle 3 speed 5 16 000 | 25° C. 30° C. 40° C. | Spindle 3 speed 5 | 17 600 18 200 21 000 | Spindle 3 speed 2.5 | 33 400 37 500 37 560 |

A composition is regarded as chemically stable when the content of active principle which it comprises does not change over time under different temperature conditions (AT, 30° C. and 40° C.).

According to the invention, the composition is regarded as stable when the content of BPO (expressed by weight with respect to the weight of the intermediate formulation) is included in the specifications ranging from 90% to 110%.

TABLE II

Chemical stability of the BPO in the intermediate formulation A5 (example 1)

| Formulation A5 | T0 | | T1 Month | T2 Months | T3 Months | T6 Months |
|---|---|---|---|---|---|---|
| % w/w BPO (HPLC) | 102 | 25° C. 30° C. 40° C. | 102.6 103.4 | 101.1 103.8 | 104.7 101.8 99.3 | 101.6 99.0 93.6 |

The composition according to the invention can additionally comprise one or more agents chosen from dispersing agents, solubilizing agents, stabilizing agents, preservatives, fatty substances, thickening agents, dyes, fragrances, surfactants, gelling agents, complexing agents, neutralizing agents, foaming emulsifying agents, nonfoaming emulsifying agents, fillers, sequestering agents, reducing agents, odor maskers, plasticizing agents, softening agents, moisturizing agents, pigments, clays, inorganic fillers, inorganic colloids, polymers, proteins, pearlescent agents, waxes, oils, such as, for example, paraffins or silicones, fatty acids, solid esters of fatty alcohol or of fatty acids, gums or wetting agents.

Water-soluble dyes, such as FD&C Blue 1 (of empirical formula $C_{37}H_{34}N_2Na_2O_9S_3$), and fat-soluble dyes, such as Sudan Red III or Nile Red, exhibit the advantage of coloring one of the formulation intermediates. This coloring makes it possible to monitor the satisfactory mixing of the two formulation intermediates and to set off the formation of the foam. This coloring is presented in particular in the examples and in FIG. 1.

Gelling Agents for the Intermediate Formulation Comprising the Gas Activator

The intermediate composition A preferably comprising at least one gas-activating agent preferably comprises at least one gelling agent and/or suspending agent.

Gels comprising BPO are known to be very complicated to stabilize. The viscosity and the suspending power of these formulations are often hard to guarantee over time. Furthermore, the formulation A can comprise large amounts of acid and electrolytes.

Mention may be made, as nonlimiting examples of gelling agents and/or suspending agents which are resistant simultaneously to BPO, to electrolytes and to acidic pH values and which can be present in the compositions A according to the invention, of ready-for-use mixtures, such as Polyacrylate-13 & Polyisobutene & Polysorbate 20 sold by Seppic under the name Sepiplus 400®, polysaccharides with, as nonlimiting examples, xanthan gum, such as Xantural 180® sold by Kelco, gellan gum sold under the name of Kelcogel® by Kelco, Sclerotium Gum sold under the name Amigel® by Alban Muller Industrie, guar gum and its derivatives, such as Hydroxypropyl Guar sold under the name Jaguar HP-105® by Rhodia, cellulose and its derivatives, such as microcrystalline cellulose and sodium carboxymethyl cellulose sold under the name Blanose CMC 7H4XF® by Hercules, hydroxypropylmethylcellulose, in particular the product sold under the name of Methocel E4M® Premium by Dow Chemical, or hydroxyethylcellulose, in particular the product sold under the name of Natrosol HHX 250® by Aqualon, the family of the magnesium aluminum silicates, such as Veegum K®, Veegum Plus® or Veegum Ultra® sold by Vanderbilt, the family of the modified starches, such as the modified potato starch sold under the name of Structure Solanace®, the family of the carrageenans, in particular divided into four main families: κ, λ, β and ω, such as the Viscarin® and Gelcarin® products sold by IMCD. Or else Polyvinyl Alcohol, also known under the abbreviation PVA, sold by Merck under the name POLYVINYL ALCOHOL 40-88®. Preferably, Veegum K® and Xantural 180® will be used in combination.

The gelling agent as described above can be used at the preferred concentrations ranging from 0.001% to 15% and more preferably ranging from 0.15% to 5% by weight, with respect to the weight of the intermediate formulation A.

Gelling Agents for the Intermediate Formulation Comprising the Gas Generator

The intermediate composition B preferably comprising at least one gas-generating agent preferably comprises at least one gelling agent and/or suspending agent.

Mention may be made, as nonlimiting examples of gelling agents and/or suspending agents which are resistant both to electrolytes and to basic pH values and which can participate in the intermediate compositions B according to the invention, of acrylic acid polymers, such as Acrylates/C10-30 Alkyl Acrylate Crosspolymer, for example the carbomers described as insensitive to electrolytes sold under the name of Ultrez 20®, Ultrez 10®, Carbopol 1382®, Carbopol ETD2020NF® or Aqua SF1® by Lubrizol, the Ammonium Acrylate/Acrylamide Copolymer & Polyisobutene & Polysorbate 20 mixture sold by Seppic under the name Sepiplus 265®, polysaccharides with, as nonlimiting examples, xanthan gum, such as Xantural 180® sold by Kelco, gellan gum sold under the name of Kelcogel® by Kelco, Sclerotium Gum sold under the name Amigel® by Alban Muller Industrie, guar gum and its derivatives, such as Hydroxypropyl Guar sold under the name Jaguar HP-105® by Rhodia, cellulose and its derivatives, such as microcrystalline cellulose and sodium carboxymethyl cellulose sold under the name Blanose CMC 7H4XF® by Hercules, hydroxypropylmethylcellulose, in particular the product sold under the name of Methocel E4M Premium® by Dow Chemical, or hydroxyethylcellulose, in particular the product sold under the name of Natrosol HHX 250® by Aqualon, the family of the magnesium aluminum silicates, such as Veegum K®, Veegum Plus® or Veegum Ultra® sold by Vanderbilt, the family of the modified starches, such as the modified potato starch sold under the name of Structure Solanace® or the tapioca flour starch known under the name of Naviance Tapioca P® sold by Akzo Nobel, or the family of the carrageenans, in particular divided into four main families: κ, λ, β and ω, such as the Viscarin® and Gelcarin® products sold by IMCD.

The gelling agent as described above can be used at the preferred concentrations ranging from 0.001% to 15% and more preferably ranging from 0.15% to 5% by weight, with respect to the weight of the intermediate formulation B.

Wetting Agents

The composition according to the invention can comprise one or more wetting agents. In this case, this or these wetting agents are present in the intermediate composition which comprises the BPO.

Use is preferably made, among the wetting agents which have the role of reducing the surface tension and of allowing the BPO to be incorporated more easily in the formulation and mainly during the grinding thereof, without this list being limiting, of a wetting agent which can preferably exhibit an HLB of 10 to 14, compounds of the family of the Poloxamers and/or of the glycols and more particularly Synperonic PE/L44® and/or Synperonic PE/L62® and/or compounds such as propylene glycol, dipropylene glycol, propylene glycol dipelargonate, lauroglycol or ethoxydiglycol. Preferably, the wetting agents are in the liquid form, so as to be easily incorporated in the composition without it being necessary to heat it. The wetting agent which is particularly preferred is Lutrol L44® sold by BASF. It can be used at the preferred concentrations ranging from 0.001% to 5% and more preferably ranging from 0.01% to 1% by weight, with respect to the weight of the total composition.

Humectants

Use is optionally made, among the humectants and/or emollients which have the role of moisturizing the skin and of facilitating the application of the formulation, without this list being limiting, of compounds such as a polyol which is miscible with water at ambient temperature (25° C.), in particular chosen from polyols having in particular from 2 to 20 carbon atoms, preferably having from 2 to 10 carbon atoms and preferably having from 2 to 6 carbon atoms, such as glycerol, glycol derivatives, such as propylene glycol, butylene glycol, pentylene glycol, hexylene glycol, dipropylene glycol, diethylene glycol and their mixtures, but also sugars (by way of example, glucose or lactose), polyethylene glycols (PEGs) (by way of example, Lutrol E400), urea or amino acids (by way of example, serine, citrulline, arginine, asparagine or alanine).

Mention may be made, as preferred humectant and/or emollient, of glycerol and propylene glycol.

The humectants can be used, alone or in combination, at preferred concentrations ranging from 0.001% to 30% and more preferably ranging from 0.01% to 10% by weight, with respect to the weight of the total formulation.

Chelating Agents

Mention may be made, among chelating agents, as non-limiting examples, of ethylenediaminetetraacetic acid (EDTA), diethylenetriaminepentaacetic acid (DTPA), ethylenediamined(o-hydroxyphenylacetic acid) (EDDHA), (2-hydroxyethyl)ethylenediaminetriacetic acid (HEDTA), ethyldiamined(o-hydroxy-p-methylphenylacetic acid) (EDDHMA) and ethylenediamined(5-carboxy-2-hydroxyphenylacetic acid) (EDDCHA).

Mention may be made, as preferred chelating agent, of ethylenediaminetetraacetic acid (EDTA), sold in particular under the name Titriplex III®. It can be used at the preferred concentrations ranging from 0.001% to 1% and more preferably from 0.05% to 0.1% by weight, with respect to the weight of the total formulation.

Cosmetic Active Principles

The composition according to the invention can comprise one or more cosmetic active principles, such as, for example, without implied limitation, allantoin with anti-irritant properties, antiacneic zinc gluconate, dipotassium glycyrrhizate for its anti-inflammatory properties or else healing α-bisabolol.

Fillers and Particles

Fillers and/or particles can be used to stabilize and boost the foam. Some of them have the specific property of being positioned at the water/air interface and of thus stabilizing this interface. Mention may be made, as fillers, of talc, metal oxides, such as zinc oxide or titanium dioxide $TiO_2$ T2000 sold by Merck under the name Eusolex® T-2000, clays, such as Laponites®, Bentones® or Bentonites®, but also cellulose ethers, such as Methocel K100 LV® sold by Dow, or silicas, such as Aerosil® R972 sold by Evonik or Silica HDK® H13L sold by Wacker. They can be used at concentrations ranging from 0.01% to 10% by weight, with respect to the weight of the total formulation.

The Oils of the Fatty Phase

The composition according to the invention can also comprise a fatty phase.

This fatty phase can comprise, for example, vegetable, mineral, animal or synthetic waxes, oils or butters, silicone oils and mixtures thereof.

The fatty phase can be present in one and/or other of the intermediate compositions A and B. However, due to the instability of the BPO with regard to lipophilic molecules, when the composition according to the invention comprises a fatty phase, the latter is preferably present in the intermediate composition B.

The fatty phase of the composition according to the invention can comprise, for example, vegetable, mineral, animal or synthetic oils, silicone oils and their mixtures.

Mention may be made, as examples of mineral oil, for example, of liquid paraffins of different viscosities, such as Primol 352®, Marcol 82® and Marcol 152® sold by Esso.

Mention may be made, as vegetable oil, of sweet almond oil, palm oil, soybean oil, sesame oil, sunflower oil or olive oil.

Mention may be made, as animal oil or its substitute of vegetable origin, of lanolin, squalene or fish oil with, as derivative, the perhydrosqualene sold under the name Sophiderm® by Sophim.

Mention may be made, as synthetic oil, of an ester such as cetearyl isononanoate, such as the product sold under the name of Cetiol SN PH® by Cognis France, isononyl isononanoate, such as DUB ININ® sold by Stéarinerie Dubois, diisopropyl adipate, such as the product sold under the name of Crodamol DA® by Croda, isopropyl palmitate, such as the product sold under the name of Crodamol IPP® by Croda, or caprylic/capric triglyceride, such as Miglyol 812® sold by Univar. Mention may be made, as hydrogenated polyisobutene, of the Parleam® products sold by Rossow.

Mention may be made, as silicone oil, of a dimethicone, such as the product sold under the name of Q7-9120 Silicone Fluid®, with a viscosity of 20 cSt to 12 500 cSt, by Dow Corning, or of a cyclomethicone, such as the product sold under the name of ST-Cyclomethicone 5NF®, also by Dow Corning, or else DC 9045 Elastomer Blend®, also by Dow Corning.

The fatty phases can, according to the pharmaceutical dosage form of each formulation intermediate, be present in contents ranging from 0% to 95% by weight, with respect to the weight of each intermediate formulation.

Non-Liquid Fatty Substances

The composition according to the invention can also comprise solid fatty substances, such as natural or synthetic waxes, fatty acids, such as stearic acid, fatty alcohols, such as Speziol C18 Pharma or Speziol C16® sold by Cognis, and texturing agents of tribehenate type, such as Compritol 888® sold by Gattefosse, or hydrogenated castor oils, such as Cutina HR sold by Cognis, or glyceryl stearate, such as Geleol® sold by Gattefosse. These nonliquid fatty substances can be used alone or as a mixture from 0% to 30% by weight, with respect to the weight of the total formulation. However, an exceptional foam quality has been observed when fatty alcohols of formula $CH_3(CH_2)_nOH$ (n is between 11 and 23) are present at contents of greater than 1% by weight, with respect to the weight of the total formulation.

Nonionic Emulsifiers

The composition according to the invention can also comprise nonionic emulsifiers. The latter are in particular present in the intermediate formulation or formulations which comprise a fatty phase (emulsions).

Mention may be made, as preferred emulsifiers, of hydrophilic emulsifiers such as Glyceryl Stearate (and) PEG-100 Stearate sold under the name Arlacel 165FL® by Uniquema, lipophilic emulsifiers such as Glucate SS® and Glucamate SSE®, Polyoxyethylene (21) Stearyl Ether sold under the name Brij 721® by Uniquema or else in the same family Brij S2® and Brij S20®. The self-emulsifying wax sold by Croda under the name of Polawax NF®. Mention may also made of nonionic surfactants exhibiting a high HLB, sorbitan esters, such as POE(20) sorbitan monooleate sold under the name of Tween 80® (HLB=15), POE(20) sorbitan monostearate sold under the name of Tween 60® (HLB=14.9), fatty alcohol ethers, such as POE (21) stearyl ether (HLB=15.5), or ceteareth-20 sold under the name of Eumulgin® B2 PH by Cognis (HLB of 15.5), or of nonionic surfactants with a low HLB, sorbitan esters, such as sorbitan monostearate (sold under the name of Span 60 by Uniquema), glycerol esters, such as glycerol monostearate (Cutina GMS from Cognis), or sucrose esters with a low HLB, such as sucrose distearate. In another form according to the invention, the surfactants which can be used are polyglycerol esters. They are esters of polyglycerolated fatty acids obtained by condensation of glycerol. Glycolipid emulsifiers, such as Montanov 202® sold by Seppic. Some emulsifiers can be sold in the form of a mixture, such as the Emulium Kappa® and Emulium Delta® products sold by Gattefosse. These surfactants can be used alone or in combination, so that the HLB of the system is greater than 12 and preferably greater than 15.

Such emulsifiers can be used between 0.01% and 30% by weight, with respect to the weight of the total composition, preferably between 0.1% and 15% and more preferably between 0.5% and 7%.

Preservative of the Composition B

Mention may be made, as examples of preservatives, of benzalkonium chloride, bronopol, chlorhexidine, chlorocresol and its derivatives, ethyl alcohol, phenoxyethanol, potassium sorbate, diazolidinyl urea, benzyl alcohol, parabens, sodium benzoate or their mixtures.

Mention may be made, as preferred preservative system, of the phenoxyethanol and pentylene glycol combination.

Cleaning Agents of the Composition B

In a specific form, the composition B comprising the gas-generating agent is a cream devoid of foaming surfactant and contains nonfoaming cleaning agents which, by themselves alone, are not capable of generating foam, such as Disodium PEG-12 Dimethicone Sulfosuccinate sold by Rhodia under the name of Mackanate® Ultra-SI, Sodium Cocoamphoacetate or Disodium Cocoamphodiacetate sold by Evonik under the name Rewoteric AMC® or Rewoteric AM2CNM®, or sugar esters, such as those sold by Sisterna under the name PS750-C® or SP70-C®. The amounts of these cleaning agents are between 0% and 1% by weight, with respect to the total weight of the formulation B.

Foaming Surfactants of the Composition B

In another specific form, the composition B comprising the gas-generating agent is a gel or a cream and comprises a small amount of foaming surfactants.

The applicant company has known how to select a foaming surfactant which is stable over time in the presence of a high concentration of sodium bicarbonate. The following surfactants were tested in the mixture: Sodium C14-C16 Olefin Sulfonate sold by Clariant under the name Hostapur® OSB or else Hostapur® OS Liq but also Nansa® LSS 495-H sold by Huntsman, Rodacal LSS 80 RPB from Rhodia, BIO-Terge® AS-90 beads from Stepan, Sodium Cocoyl Glycinate sold by Clariant under the name Hostapon® SG, Sodium Cocoyl Isethionate sold by Clariant under the name Hostapon® SCI85 G, Sodium Lauroyl Methyl Isethionate sold by Innospec under the name Iselux® LG, Decyl Glucoside sold by Cognis under the name Plantacare® 2000 Up, Zinc Coceth Sulfate sold by Zschimmer & Schwarz under the name Zetesol® Zn, Glyceryl Monolaurate sold by Rossow under the name POEM® DL 100, and Disodium PEG-5 Laurylcitrate Sulfosuccinate sold by Evonik under the name Rewopol SB C55®.

Among the foaming surfactants incorporated in the formulation intermediate B, the only one which retained its foaming properties and its organoleptic properties (such as the color or the odor) is Sodium C14-16 Olefin Sulfonate.

The amounts of this foaming surfactant can be between 0% and 1% by weight, with respect to the weight of the total formulation.

The following examples illustrate the invention without restricting the scope thereof.

EXAMPLES

Example 1: Examples of Formulations

Examples of Formulations A: Intermediate Compositions A Comprising the Gas-Activating Agent The intermediate formulations A were prepared according to the following process:

Stage 1: The gelling agents and then the agent or agents which activate the gas generator are added with stirring to the main water phase at a temperature of greater than 60° C.

Stage 2: At the same time, the grinding phase comprising the BPO, water, propylene glycol and Poloxamer 124 is carried out under high shear.

Stage 3: The compositions resulting from stages 1 and 2 are mixed at a temperature of less than 30° C.

Stage 4: The additives, such as the dye Blue 1, pure or in solution, are added.

In the examples of formulations below, the amounts are expressed as percentages with respect to the weight of the intermediate formulation and not with respect to the weight of the total formulation (total formulation is understood to mean the mixture of the two intermediate formulations).

Example A1

| Ingredients | INCI Name | % |
| --- | --- | --- |
| WATER | WATER | q.s. for 100 |
| TITRIPLEX III ® | DISODIUM EDTA | 0.1 |
| VEEGUM K ® | MAGNESIUM ALUMINUM SILICATE | 2 |
| XANTURAL 180 ® | XANTHAN GUM | 0.7 |
| BLANOSE CMC 7H4XF PHARM ® | CELLULOSE GUM | 0.4 |
| CITRIC ACID MONOHYDRATE | CITRIC ACID | 3 |
| SODIUM CITRATE, TRISODIUM SALT | SODIUM CITRATE | 0.8 |
| LUTROL L44 ® | POLOXAMER 124 | 0.2 |
| PROPYLENE GLYCOL | PROPYLENE GLYCOL | 4 |
| BPO | BENZOYL PEROXIDE | 5.2 |

Example A2

| Ingredients | INCI Name | % |
| --- | --- | --- |
| WATER | WATER | q.s. for 100 |
| TITRIPLEX III ® | DISODIUM EDTA | 0.1 |
| GRANULATED AMIGEL | SCLEROTIUM GUM | 1 |
| XANTURAL 180 ® | XANTHAN GUM | 0.3 |
| BLANOSE CMC 7H4XF ® PHARM | CELLULOSE GUM | 0.4 |
| CITRIC ACID MONOHYDRATE | CITRIC ACID | 3 |
| SODIUM CITRATE TRIHYDRATE | SODIUM CITRATE | 0.8 |
| LUTROL L44 ® | POLOXAMER 124 | 0.2 |
| PROPYLENE GLYCOL | PROPYLENE GLYCOL | 4 |
| BPO | BENZOYL PEROXIDE | 5.2 |

Example A3

| Ingredients | INCI Name | % |
| --- | --- | --- |
| WATER | WATER | q.s. for 100 |
| SATIAXANE UCX 911 ® | XANTHAN GUM | 0.6 |
| VEEGUM K ® | MAGNESIUM ALUMINUM SILICATE | 2.5 |
| CITRIC ACID MONOHYDRATE | CITRIC ACID | 3.6 |
| SODIUM CITRATE, TRISODIUM SALT | SODIUM CITRATE | 2.6 |
| LUTROL L44 ® | POLOXAMER 124 | 0.2 |
| BPO | BENZOYL PEROXIDE | 10 |
| PROPYLENE GLYCOL | PROPYLENE GLYCOL | 4.0 |

Example A4

| Ingredients | INCI Name | % |
| --- | --- | --- |
| WATER | WATER | q.s. for 100 |
| SATIAXANE UCX 911 ® | XANTHAN GUM | 0.7 |
| VEEGUM K ® | MAGNESIUM ALUMINUM SILICATE | 2.5 |
| FD&C BLUE 1 | FD&C BLUE 1 | 0.0003 |
| DISODIUM PYROPHOSPHATE | DISODIUM PYROPHOSPHATE | 12 |
| LUTROL L44 ® | POLOXAMER 124 | 0.2 |
| BPO | BENZOYL PEROXIDE | 5.2 |
| PROPYLENE GLYCOL | PROPYLENE GLYCOL | 4.0 |

Example A5

| Ingredients | INCI Name | % |
| --- | --- | --- |
| WATER | WATER | q.s. for 100 |
| TITRIPLEX III ® | DISODIUM EDTA | 0.1 |
| SATIAXANE UCX 911 | XANTHAN GUM | 0.7 |
| VEEGUM K ® | MAGNESIUM ALUMINUM SILICATE | 2.5 |
| DISODIUM PYROPHOSPHATE | DISODIUM PYROPHOSPHATE | 6 |
| CITRIC ACID MONOHYDRATE | CITRIC ACID | 1.8 |
| SODIUM CITRATE, TRISODIUM SALT | SODIUM CITRATE | 1.3 |
| LUTROL L44 ® | POLOXAMER 124 | 0.2 |
| BPO | BENZOYL PEROXIDE | 5.2 |
| PROPYLENE GLYCOL | PROPYLENE GLYCOL | 4.0 |

Example A6

| Ingredients | INCI Name | % |
| --- | --- | --- |
| WATER | WATER | q.s. for 100 |
| TITRIPLEX III ® | DISODIUM EDTA | 0.1 |
| SATIAXANE UCX 911 ® | XANTHAN GUM | 0.7 |
| VEEGUM K ® | MAGNESIUM ALUMINUM SILICATE | 2.5 |
| DISODIUM PYROPHOSPHATE | DISODIUM PYROPHOSPHATE | 8.4 |
| CITRIC ACID MONOHYDRATE | CITRIC ACID | 1.4 |
| SODIUM CITRATE, TRISODIUM SALT | SODIUM CITRATE | 1 |
| LUTROL L44 ® | POLOXAMER 124 | 0.2 |
| BPO | BENZOYL PEROXIDE | 5.2 |
| PROPYLENE GLYCOL | PROPYLENE GLYCOL | 4.0 |
| FD&C BLUE 1 | FD&C BLUE 1 | 0.0005 |

Example A7

| Ingredients | INCI Name | % |
|---|---|---|
| WATER | WATER | QSP 100 |
| TITRIPLEX III ® | DISODIUM EDTA | 0.1 |
| SATIAXANE UCX 911 ® | XANTHAN GUM | 0.7 |
| VEEGUM K ® | MAGNESIUM ALUMINUM SILICATE | 2.5 |
| PROBENZ SP ® | SODIUM BENZOATE | 0.2 |
| DISODIUM PYROPHOSPHATE | DISODIUM PYROPHOSPHATE | 7.2 |
| CITRIC ACID MONOHYDRATE | CITRIC ACID | 1.4 |
| SODIUM CITRATE TRISODIQUE | SODIUM CITRATE | 1 |
| LUTROL L44 ® | POLOXAMER 124 | 0.2 |
| BPO | BENZOYL PEROXIDE | 5.2 |
| PROPYLENE GLYCOL | PROPYLENE GLYCOL | 4.0 |

Example A8

| Ingredients | INCI Name | % |
|---|---|---|
| WATER | WATER | q.s. for 100 |
| TITRIPLEX III ® | DISODIUM EDTA | 0.1 |
| SATIAXANE UCX 911 ® | XANTHAN GUM | 0.7 |
| VEEGUM K ® | MAGNESIUM ALUMINUM SILICATE | 2.5 |
| PROBENZ SP ® | SODIUM BENZOATE | 0.2 |
| SODIUM DIHYDROGENPHOSPHATE | SODIUM PHOSPHATE | 6.2 |
| PHENOXETHOL ® | PHENOXYETHANOL | 0.5 |
| CITRIC ACID MONOHYDRATE | CITRIC ACID | 1.5 |
| SODIUM CITRATE, TRISODIUM SALT | SODIUM CITRATE | 0.5 |
| LUTROL L44 ® | POLOXAMER 124 | 0.2 |
| BPO | BENZOYL PEROXIDE | 5.2 |
| PROPYLENE GLYCOL | PROPYLENE GLYCOL | 4.0 |

Examples of Formulations B: Intermediate Compositions B Comprising the Gas-Generating Agent The intermediate formulations B were prepared according to the following process:

Stage 1': The gelling agents are added with stirring to the main water phase at a temperature of greater than 60° C.

Stage 2': The cleaning or foaming agents and also the additives, such as the preservatives, are added at an appropriate temperature.

Stage 3': The mixture is neutralized.

Stage 4': The sodium bicarbonate is added at a temperature of less than 40° C.

In a specific form, a fatty phase (comprising the oils, the waxes and the surfactants) can be heated to a temperature of greater than 60° C. and incorporated in the main phase after stage 1'.

Formulation B1

| Ingredients | INCI Name | % |
|---|---|---|
| WATER | WATER | q.s. for 100 |
| VEEGUM K ® | MAGNESIUM ALUMINUM SILICATE | 2.5 |
| SATIAXANE UCX 911 ® | XANTHAN GUM | 0.5 |
| TITRIPLEX III ® | DISODIUM EDTA | 0.1 |
| PLANTACTIV PGL ® | DIPOTASSIUM GLYCYRRHIZATE | 0.5 |
| ZINC GLUCONATE ® | ZINC GLUCONATE | 0.4 |
| HOSTAPUR OSB ® | (C14-16) SODIUM OLEFIN SULFONATE | 2 |
| NaOH, 10% IN AQ. SOL. | SODIUM HYDROXIDE | 1 |
| SODIUM BICARBONATE | SODIUM HYDROGENCARBONATE | 5 |
| PHENOXYETHANOL | PHENOXYETHANOL | 1 |
| HYDROLITE 5 | PENTYLENE GLYCOL | 5 |

Formulation B2

| Ingredients | INCI Name | % |
|---|---|---|
| WATER | WATER | q.s. for 100 |
| VEEGUM K ® | MAGNESIUM ALUMINUM SILICATE | 2.5 |
| SATIAXANE UCX 911 ® | XANTHAN GUM | 0.6 |
| TITRIPLEX III ® | DISODIUM EDTA | 0.1 |
| PLANTACTIV PGL ® | DIPOTASSIUM GLYCYRRHIZATE | 0.5 |
| ZINC GLUCONATE | ZINC GLUCONATE | 0.4 |
| EUMULGIN B2 ® | CETEARETH-20 | 3 |
| MACKAMATE ULTRA-SI ® | DISODIUM PEG-12 DIMETHICONE SULFOSUCCINATE | 2 |
| PROBENZ ® | POTASSIUM SORBATE | 0.5 |
| PARLEAM ® | HYDROGENATED POLYISOBUTENE | 6 |
| SPEZIOL C16-C18 ® | CETEARYL ALCOHOL | 7 |
| NaOH, 10% IN AQ. SOL. | SODIUM HYDROXIDE | 1 |
| SODIUM BICARBONATE | SODIUM HYDROGENCARBONATE | 5 |
| PHENOXYETHANOL | PHENOXYETHANOL | 1 |

Formulation B3

| Ingredients | INCI Name | % |
|---|---|---|
| WATER | WATER | q.s. for 100 |
| VEEGUM K ® | MAGNESIUM ALUMINUM SILICATE | 2.5 |
| SATIAXANE UCX 911 ® | XANTHAN GUM | 0.6 |
| TITRIPLEX III ® | DISODIUM EDTA | 0.1 |
| PLANTACTIV PGL ® | DIPOTASSIUM GLYCYRRHIZATE | 0.5 |
| ZINC GLUCONATE | ZINC GLUCONATE | 0.4 |
| EUMULGIN B2 ® | CETEARETH-20 | 3 |
| MACKAMATE ULTRA-SI ® | DISODIUM PEG-12 DIMETHICONE SULFOSUCCINATE | 2 |
| PROBENZ ® | POTASSIUM SORBATE | 0.5 |
| PARLEAM ® | HYDROGENATED POLYISOBUTENE | 6 |
| SPEZIOL C16-C18 ® | CETEARYL ALCOHOL | 7 |
| NaOH, 10% IN AQ. SOL. | SODIUM HYDROXIDE | 1 |
| SODIUM CARBONATE | SODIUM CARBONATE | 5 |
| PHENOXYETHANOL | PHENOXYETHANOL | 1 |

The mixtures in a 1:1 ratio by weight of the intermediate compositions A and B described above are represented in the table below. A cross at the intersection of two formulation intermediates indicates that the mixture is possible and generates a foam with the desired properties.

|         | Formulo B |    |    |
|---------|-----------|----|----|
| Formulo A | B1 | B2 | B3 |
| A1 | X | X | X |
| A2 | X | X | X |
| A3 | X | X | X |
| A4 | X | X | X |
| A5 | X | X | X |
| A6 | X | X | X |
| A7 | X | X | X |

Example 2: Measurements of Density

Starting from the examples of formulations described in example 1, measurements of foam density were carried out at the time at which the 2 intermediate formulations A and B are brought into contact (T0) and then when the chemical reaction generated by bringing the two compositions into contact has finished:
a)
Density formulation A5=1.108
Density formulation B1=1.052
Foam A5/B1 (50/50)=0.251

The measurement of the density of the foam shows that the volume has been increased by a factor of 5 and has been confirmed by the photographs in FIG. 1. The left-hand photograph represents the time of the mixing (T0) and the right-hand photograph represents the foam obtained when the acid/base chemical reaction is complete.
b)
Density formulation A5=1.108
Density formulation B2=1.012
Foam A5/B2 (50/50)=0.340

Figure 2:
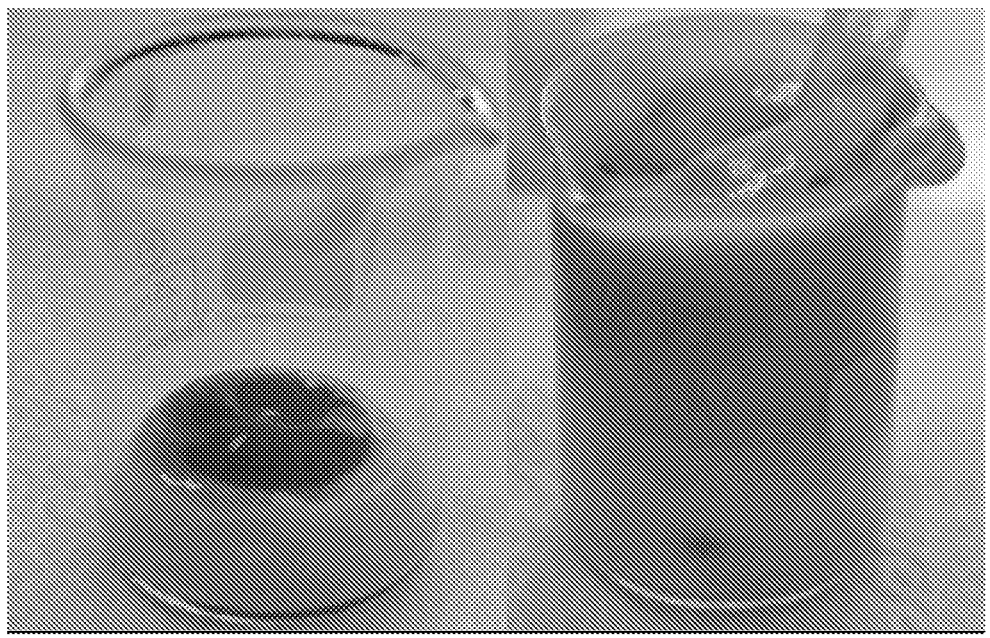
FIG. 2 shows photographs of a second composition in accordance with the invention obtained by mixing the two intermediate compositions A5 and B2 described in the examples, immediately after mixing these compositions and then when the reaction between these two compositions is complete (maximum volume of foam).

The measurement of the density of the foam shows that the volume has been increased by a factor of 3 and has been confirmed by the photographs in FIG. 2. The left-hand photograph represents the time of the mixing (T0) and the right-hand photograph represents the foam obtained when the acid/base chemical reaction is complete.

Example 3: Comparative Study of Measurement of Irritation

Study Protocol.

The study is carried out according to the OECD TG 439 protocol in force for the short application time (contact time RHE/product 15 min). This protocol is appropriate for a long application time (contact time RHE/product 18 h).

The objective of this study is to evaluate the tolerance of the supports of the complete and intermediate formulations on reconstructed human epidermi (RHE, Episkin model) through:
- the evaluation of the reduction of MTT (cell viability)
- the measurement of the release of IL-la (marker for irritation)

The formulations tested are:
- an intermediate composition of acidic formulation: example A7 placebo (that is to say, not comprising BPO) uncolored (that is to say, not comprising dye),
- an intermediate composition of basic formulation: example B1,
- an intermediate composition of basic formulation: example B2,
- the complete formulation 1 composed of the mixture: A7 placebo+B1 (in a 50/50 ratio by weight),
- the complete formulation 2 composed of the mixture: A7 placebo+B2 (in a 50/50 ratio by weight),
- a commercial reference in the form of a cleaning gel.

Results of the Study:

| Mixture tested | Short exposure Viability (%) | Long exposure Viability (%) | Conclusion Irritant potential |
|---|---|---|---|
| B1 | 92.5 | 59.6 | Non-irritant |
| A7 placebo | 86.0 | 84.5 | Non-irritant |
| Complete formulation 1 | 93.2 | 86.8 | Non-irritant |
| Complete formulation 2 | 95.8 | 83.4 | Non-irritant |
| Commercial ref. | 76.6 | 6.7 | Potentially irritating |

| Test item | Short exposure IL-1α vs control | Long exposure IL-1α vs control | Conclusion Irritant potential |
|---|---|---|---|
| B1 | 5.5 | 30.6 | Non-irritant |
| A7 placebo | 2.2 | 2.3 | Non-irritant |
| Complete formulation 1 | 4.5 | 11.6 | Non-irritant |
| Complete formulation 2 | 1.9 | 3.1 | Non-irritant |
| Commercial ref. | 6.2 | 113.9 | Potentially irritating |

The measurements of the MTT according to the OECD protocol in force indicate that the rinse-off "Complete formulations" tested are non-irritant, whereas the "Commercial ref." is potentially irritating.

Furthermore, the assaying of IL-la after application at long and short exposure times of the complete formulations shows a much lower level of irritation markers with regard to the foam formulations than after application of the commercial reference.

Example 4

The ideal content of citric acid, sodium pyrophosphate and sodium dihydrogenphosphate monohydrate for reacting with 5% of sodium bicarbonate has been established empirically. The values are expressed as percentages weight/weight with respect to the weight of each of the two intermediate formulations.

|  | Ratio 1 | Ratio 2 | Ratio 3 |
|---|---|---|---|
| Sodium bicarbonate | 5% | 5% | 5% |
| Citric acid | 3.5% | — | — |
| Disodium pyrophosphate | — | 12% | — |
| Sodium dihydrogenphosphate monohydrate | — | — | 7.2% |

In order for the pH of the formulation comprising the gas activator to exhibit an optimum compatibility with the skin, sodium citrate has been added in order to create a citric acid/sodium citrate buffer.

A portion of the citric acid/sodium citrate buffer can advantageously be replaced with disodium pyrophosphate and vice versa, according to the contents cited by way of example in table Iii below:

TABLE III

The values are expressed as percentages weight/weight with respect to the weight of each of the two intermediate formulations.

|  | E1 | E2 | E3 | E4 | E5 | E6 | E7 |
|---|---|---|---|---|---|---|---|
| Sodium bicarbonate | 5% | 5% | 5% | 5% | 3% | 3% | 3% |
| Citric acid | 3.5% | 1.75% | 1.4% | 0 | 2.1% | 1.05% | 0 |
| Sodium citrate | 2.7% | 1.3% | 1% | 0 | 1.6% | 1.15% | 0 |
| Disodium pyrophosphate | 0 | 6% | 7.2% | 12% | 0 | 3.6% | 7.2% |

A portion of the citric acid/sodium citrate buffer can advantageously be replaced with sodium dihydrogenphosphate monohydrate and vice versa, according to the contents cited by way of example in table IV below:

TABLE IV

The values are expressed as percentages weight/weight with respect to the weight of each of the two intermediate formulations.

|  | E1 | E8 | E9 |
|---|---|---|---|
| Sodium bicarbonate | 5% | 5% | 5% |
| Citric acid | 3.5% | 1.5% | 0 |
| Sodium citrate | 2.7% | 0.5% | 0 |
| Sodium dihydrogenphosphate monohydrate | 0 | 6.2% | 10% |

In a specific form, it has been determined that, when the amount of citric acid is greater than or equal to 1.4, the amount of foam is optimal when the disodium pyrophosphate is present in the composition according to the following equation:

$$[C]=2.4[B]-2.4[A]/0.7$$

when:
[C]=content by weight of disodium pyrophosphate in the intermediate composition A
[A]=content by weight of citric acid monohydrate in the intermediate composition A
[B]=content by weight of sodium bicarbonate in the intermediate composition B The equation above thus makes it possible to calculate the optimum contents between the sodium bicarbonate, the citric acid and the sodium pyrophosphate.

The invention claimed is:

1. A foam composition obtained by combining:
   (a) a composition A comprising an agent which activates a gas-generating agent selected from the group consisting of an acid, a partially salified polyacid salt, a buffer solution of weak acid and of its conjugate base, and the mixtures thereof, and
   (b) a composition B comprising (i) a gas-generating agent selected from the group consisting of sodium bicarbonate, potassium bicarbonate, sodium carbonate, potassium carbonate and mixtures thereof and (ii) one or more foaming surfactants are selected from the group consisting of sodium C14-C16 olefin sulfonate, sodium cocoyl glycinate, sodium cocoyl isethionate, sodium lauroyl methyl isethionate, decyl glucoside, zinc coceth sulfate, glyceryl monolaurate, and disodium PEG-5 laurylcitrate sulfosuccinate,
   wherein compositions A and/or B comprise benzoyl peroxide, and
   wherein the one or more foaming surfactants are present in an amount of at most 1%, by weight, with respect to the weight of the total composition.

2. The composition as defined by claim 1, wherein the composition A comprises benzoyl peroxide.

3. The composition as defined by claim 1, wherein the foam composition is self-foaming.

4. The composition as defined by claim 1, wherein the gas generating agent is sodium bicarbonate.

5. The composition as defined by claim 1, wherein the gas generated from the gas-generating agent is carbon dioxide ($CO_2$).

6. The composition as defined by claim 1, wherein the gas-generating agent is present in an amount ranging from 1% to 10% by weight, with respect to the weight of the intermediate composition B.

7. The composition as defined by claim 6, wherein the gas generating agent is present in an amount of from 2% to 8% by weight.

8. The composition as defined by claim 1, wherein the composition B has a basic pH.

9. The composition as defined by claim 8, wherein the basic pH is from 7 to 12.

10. The composition as defined by claim 1, wherein the agent which activates the gas-generating agent is selected from the group consisting of citric acid, tartaric acid, malic acid, lactic acid, phosphoric acid and pyrophosphoric acid, the salts of these acids, and mixtures thereof.

11. The composition as defined by claim 10, wherein the agent which activates the gas-generating agent is selected from the group consisting of a citric acid/sodium citrate buffer alone; or phosphoric acid, sodium phosphate, and disodium pyrophosphate, alone or as a mixture with citric acid/sodium citrate buffer.

12. The composition as defined by claim 10, wherein the agent which activates the gas-generating agent is a citric acid/sodium citrate buffer, alone or as a mixture with sodium phosphate and/or disodium pyrophosphate.

13. The composition as defined by claim 1, wherein the agent which activates the gas-generating agent is present in an amount ranging from 0.001% to 95% by weight, with respect to the total weight of the composition A.

14. The composition as defined by claim 1, wherein the composition A has an acidic pH.

15. The composition as defined by claim 14, wherein the acidic pH is from 1 to 6.

16. The composition as defined by claim 1, wherein the composition A is in the form of a solution, a gel or an emulsion.

17. The composition as defined by claim 16, wherein the composition A is in the form of a gel.

18. The composition as defined by claim 1, wherein the composition B is in the form of a solution, a gel or an emulsion.

19. The composition as defined by claim 18, wherein the composition B is in the form of an emulsion.

20. The composition as defined by claim 1, wherein the composition further comprises one or more active principles selected from the group consisting of emollients, humectants, agents for combating free radicals, anti-inflammatory agents, vitamins, depigmenting agents, antiacne agents, antiseborrheic agents, antifungal agents, keratolytic agents, sunscreens, slimming agents and skin-coloring agents.

21. The composition as defined by claim 1, wherein the composition further comprises one or more agents selected from the group consisting of dispersing agents, solubilizing agents, stabilizing agents, preservatives, fatty substances, thickening agents, dyes, fragrances, surfactants, gelling agents, complexing agents, neutralizing agents, foaming emulsifying agents, nonfoaming emulsifying agents, fillers, sequestering agents, reducing agents, odor maskers, plasticizing agents, softening agents, moisturizing agents, pigments, clays, inorganic fillers, inorganic colloids, polymers, proteins, pearlescent agents, waxes, oils, gums and wetting agents.

22. The composition as defined by claim 21, wherein the oils are paraffins, silicones, fatty acids or solid esters of fatty alcohol or of fatty acids.

23. The composition as defined by claim 1, formulated for topical application to the skin.

24. A cosmetic method, comprising topically administering an effective amount of the composition as defined by claim 1 to the skin of an individual human subject in need thereof.

25. A kit or single multicompartment container separately comprising:
 (a) a composition A comprising an agent which activates a gas-generating agent selected from the group consisting of an acid, a partially salified polyacid salt, a buffer solution of weak acid and of its conjugate base, and the mixtures thereof, and
 (b) a composition B comprising a gas-generating agent selected from the group consisting of sodium bicarbonate, potassium bicarbonate, sodium carbonate, potassium carbonate and mixtures thereof and (ii) one or more foaming surfactants are selected from the group consisting of sodium C14-C16 olefin sulfonate, sodium cocoyl glycinate, sodium cocoyl isethionate, sodium lauroyl methyl isethionate, decyl glucoside, zinc coceth sulfate, glyceryl monolaurate, and disodium PEG-5 laurylcitrate sulfosuccinate, wherein compositions A and/or B comprise benzoyl peroxide, and wherein the one or more foaming surfactants are present in an amount of at most 1%, by weight, with respect to the weight of the total composition.

26. The kit or single multicompartment container as defined by claim 25, wherein the kit or container are designed to simultaneously release doses of the compositions A and B according to a ratio by weight ranging from 2 doses of B per 1 dose of A to 2 doses of A per 1 dose of B.

27. The kit or single multicompartment container as defined by claim 25, wherein the kit or container are designed for mixing the compositions A and B in an AB ratio by weight ranging from 0.5 to 2.

28. The kit or single multicompartment container as defined by claim 26, wherein the ratio by weight of compositions A and B is from 2 doses of B per 1 dose of A to 3 doses of A per 2 doses of B.

29. The kit or single multicompartment container as defined by claim 26, wherein the ratio by weight of compositions A and B is 1 dose A per 1 dose of B.

30. The kit or single multicompartment container as defined by claim 27, wherein the A/B ratio is from 0.5 to 1.5.

31. The kit or single multicompartment container as defined by claim 27, wherein the A/B ratio is from 0.9 to 1.1.

32. The kit or single multicompartment container as defined by claim 27, wherein the A/B ratio is 1.

* * * * *